United States Patent [19]
Walsh

[11] Patent Number: 5,661,224
[45] Date of Patent: Aug. 26, 1997

[54] METHOD AND APPARATUS FOR SPIKING ATMOSPHERIC SAMPLES

[75] Inventor: Jonathan B. Walsh, Bayville, N.Y.

[73] Assignee: H2M Labs, Inc., Melville, N.Y.

[21] Appl. No.: 598,524

[22] Filed: Feb. 8, 1996

[51] Int. Cl.$^6$ .................................................. G01N 30/86
[52] U.S. Cl. .................................. 73/1.03; 73/1.06
[58] Field of Search ...................... 73/1 G, 23.41, 73/23.42, 863.01, 863.11, 863.21, 864.81

[56] References Cited

U.S. PATENT DOCUMENTS 4,962,042 10/1990 Morabito et al. ............... 73/23.42
5,493,923 2/1996 Balfanz et al. .

FOREIGN PATENT DOCUMENTS 6258309 9/1994 Japan ........................... 73/1 G

*Primary Examiner*—Robert Raevis
*Attorney, Agent, or Firm*—Meltzer, Lippe, Goldstein, et al.

[57] ABSTRACT

An improved atmospheric spiking method and apparatus includes an 8-port valve is located between a tube desorber and a sample concentrator. The 8-port valve, tube desorber, and sample concentrator are timed to perform the following steps:

1. Load the sorbent robe into the tube desorber.
2. Connect a reference substance source with a tube having a fixed, predetermined volume.
3. Connecting the fixed volume robe to a purge gas source at one end and to a sorbent tube to be spiked at the other end, so that a known volume of the reference substance may be spiked onto the tube.
4. Connecting the spiked sorbent robe at one end to the purge gas supply and at the other end to the sample concentrator so that the tube may be desorbed.

22 Claims, 8 Drawing Sheets

METHOD AND APPARATUS FOR SPIKING ATMOSPHERIC SAMPLES

BACKGROUND OF THE INVENTION

1. Field of the Invention

The present invention relates to environmental analysis and, more particularly, to an improved method and apparatus for spiking air sample "sorbent tubes" with reference compounds.

2. Discussion of Related Art

To analyze gas samples using, for example, a gas chromatograph or mass spectrometer, the gas to be analyzed is collected in the field. When the sample is to be tested, it is collected on tubes known as "sorbent lubes". FIG. 1 is a cross-sectional view of a conventional sorbent tube 50. The sorbent tube 50 includes a cylinder 52 having openings 54, 56 at both ends. Inside the cylinder 52 is sorbent material 58. This sorbent material may be comprised of various materials, such as activated charcoal (either tenex, a carbon based material, or otherwise). The sorbent material is used either individually or in combination with other materials. When used in combinations, the sorbent material 58 is arranged in layers (layer boundaries 59 are shown in FIG. 1) so the weakest sorbent is at the inlet opening 54, followed by progressively stronger sorbents. (In FIG. 1, the sorbent material strength is represented by the number of dots per unit area. The greater number of dots/area represents greater sorbent strength.) This allows heavier molecules (e.g., larger molecules) in the sampled gas to cling to the weaker sorbent material and lighter molecules (e.g., smaller molecules) to cling to stronger sorbent material. This traps the molecules according to the size and/or polarity of the molecules. The sorbent tube openings 54, 56 are capped with gas tight seals or fittings 60, 62.

As seen in FIG. 2, when the sample is to be analyzed, the sorbent tubes 50 are loaded onto a tube desorber 64 connected to a sample concentrator 66. The concentrator 66 is connected to an analysis device 68, such as a gas chromatograph and/or mass spectrometer device 68. The sample is removed, or "desorbed", from the sorbent tube 50 to the concentrator 66 using a purge gas such as helium or nitrogen. The sample is loaded into the sorbent tube with the weaker sorbent material closer to the sample than the stronger sorbent material. Thus, the heavier molecules cling to the weaker sorbent material and the lighter molecules pass through the weaker sorbent material and cling to the stronger sorbent material. The sample is then removed, or "desorbed", from the sorbent tubes. This is done by heating the sorbent tube 50 and applying a gas flowing, the direction opposite of that used to collect the sample. This allows the molecules to dislodge from the sorbent material 58.

Known amounts of reference substances, such as reference gases, are typically added to each sorbent tube 50 after the sample is loaded into the tube, but before the sample is desorbed. This is called "spiking" the sample. Samples are spiked for several reasons. One reason is to tune the analysis device 68; a second reason is to calibrate responses of the device 68; and a third reason is to provide internal standards and surrogate compounds. Each is briefly explained.

Regarding the first reason, a mass spectrometer may need to be "tuned" to determine if it is operating properly. The device may be tuned by analyzing one or more reference substances each having a known mass spectrum. The analysis results may be compared with a known mass spectrum to determine if the device is properly tuned.

Regarding the second and third reasons, samples of some or all of the compounds expected to be found may be analyzed to determine the characteristics of each. This permits determination of responses of compounds to be analyzed relative to internal standard compounds. During the calibration process, known amounts of compounds of interest and internal standards are analyzed. Responses of compounds and internal standards are compared. Responses for compounds of interest relative to the internal standards are determined and are referred to as response factors. For example, during a calibration, a known amount of a compound of interest (methylene chloride, for example) and a known amount of internal standard (bromochloromethene, for example) are analyzed. If the relative response of the compound of interest is one half that of the internal standard, this response may be used to determine the quantity of the compound of interest in the sample to be analyzed.

In the sample to be analyzed, concentration of the compounds of interest are unknown. Known amounts of internal standards, however, have been added to the sample prior to the analysis. The concentration of compounds of interest may be calculated using the response factors determined in the calibration step. For example, a sample is spiked with 100 ngs of bromochloromethene, and methylene chloride is detected. The amount of methylene chloride in the sample may be quantified with reference to the relative response of methylene chloride that had been determined in the calibration step. That is, if the detected methylene chloride had an analytical response equal to 100 ngs of bromochloromethene, and its relative response was one half that of bromochloromethene, the quantity of methylene chloride may be determined to be 200 ngs.

Also regarding the third reason, because known amounts of the reference substance are added to the sample, the efficiency of the desorbing process may be measured by the amount of the reference substance detected by the analytical system. This is called a surrogate compound. If, for example, only 20% was recovered of a first reference substance having a certain molecule weight, and 75% was recovered of a second reference substance having a different, higher molecular weight, it is possible that the detected gases near the molecular weight of the first reference substance may be 80% higher than measured, and the detected gases near the molecular weight of the second reference substance may be 25% higher. Alternatively, the results may show that the desorbing process was not properly performed, and the results should be questioned or suspect.

Previously, several methods have been used to spike samples. Two well known methods are: (1) using a liquid solution and (2) using a gas solution. Each is described below.

Liquid solutions include small amounts of reference substance in solution with a solvent, such as methanol. The amount of the reference substance in the solution is typically on the order of nanograms. The concentration of the solvent may be a million times higher than the compounds of interest. Reference solutions are typically added to sorbent tubes by a process "flash evaporation". This process involves heating an injection port with inert gas flow. This vaporizes the solution of compounds of interest and the solvent. This mixture is then carried onto the sorbent tube.

After the sample has been loaded onto the sorbent tube 50, a syringe is used to manually inject the reference solution onto the solution into the sorbent tube 50 through one of the seals/fittings 60, 62. This method has several drawbacks. Solvent loading of the sorbent tube can lead to various problems. For example, the detector/analyzer response may be diminished by the presence of high concentrations of any individual component of the sample. The high solvent concentrations (as much as a million times higher than the reference substance) can cause chromatography problems and may reduce the response co-eluting compounds.

Spiking a sorbent tube with a gas solution is performed as follows. First, a gas solution must be prepared. Although it is possible to purchase (or prepare) pre-mixed, high pressure canisters of gas spiking solutions, it is often a cumbersome process. Typically, a gas solution is manually mixed for each tube 50 to be spiked. These solutions are difficult to prepare because known volumes of each components of the mixture must be manually added to the solution. There may be as many as sixty or more compounds in a gas solution mix. Each of these compounds must be obtained in pure form. This process may be very expensive and time consuming. Gas mixtures go bad quickly. Some reasons for this are leaks, condensation of components, and concentration changes that occur with use, particularly when stored at or near atmospheric pressure. Another problem with gas mixtures is that it is difficult to measure known mounts of the mix. Gas volumes are usually measured with syringes or mass flow meters, both of which permit the introduction of human error.

Both methods have other drawbacks in common. Both procedures are relatively-time consuming. Typically, it may take several minutes to spike a single sorbent tube using the liquid solution method and many minutes using the gas solution method. Most of this time involves preparing the solution. Both methods adversely affect the reproducibility of the procedure because of the inaccuracies involving the technique (both human and hardware errors). The inaccuracy of these methods reduce the reliability of he analysis results. Another drawback caused by both liquid and gas solutions is that manual injection introduces opportunities or human and/or hardware errors, making it difficult or impossible to precisely control the mount of solution injected into the sorbent tube. As described above, however, precision is desired because the analysis often depends on the mount of the reference substance present in the sorbent tube, particularly when spiking for internal standards and surrogate compounds.

Therefore, it is an object of the present invention to provide a method and apparatus for spiking a sorbent tube with a precisely measured mount of reference substance.

It is another object of the present invention to provide a method and apparatus for spiking a sorbent tube in a highly reproducible manner.

It is yet another object of the present invention to provide a method and apparatus for quickly spiking a sorbent tube with a substance.

It is yet even another object of the present invention to provide a method and apparatus having a high percentage of accuracy.

SUMMARY OF THE INVENTION

These and other objects of the present invention are provided by an improved atmospheric sample spiking method and apparatus. An 8-port valve is located between a tube desorber and a sample concentrator. The 8-port valve, tube desorber, and sample concentrator are timed to perform the following steps:

1. Load the sorbent tube into the tube desorber.
2. Connect a reference substance source with a tube having a fixed, predetermined volume. The fixed volume tube is filled with the reference substance.
3. Connect the fixed volume tube to a purge gas source at one end and to a sorbent tube to be spiked at the other end, so that a known volume of the reference substance is spiked onto the sorbent tube.
4. Connect the spiked sorbent tube to the purge gas supply at one end and the sample concentrator at the other end to desorb the tube.

BRIEF DESCRIPTION OF THE DRAWINGS

These and other features other present invention will become apparent from the following detailed description, in conjunction with the following drawings, wherein.

DETAILED DESCRIPTION OF A PREFERRED EMBODIMENT

Figure 3:
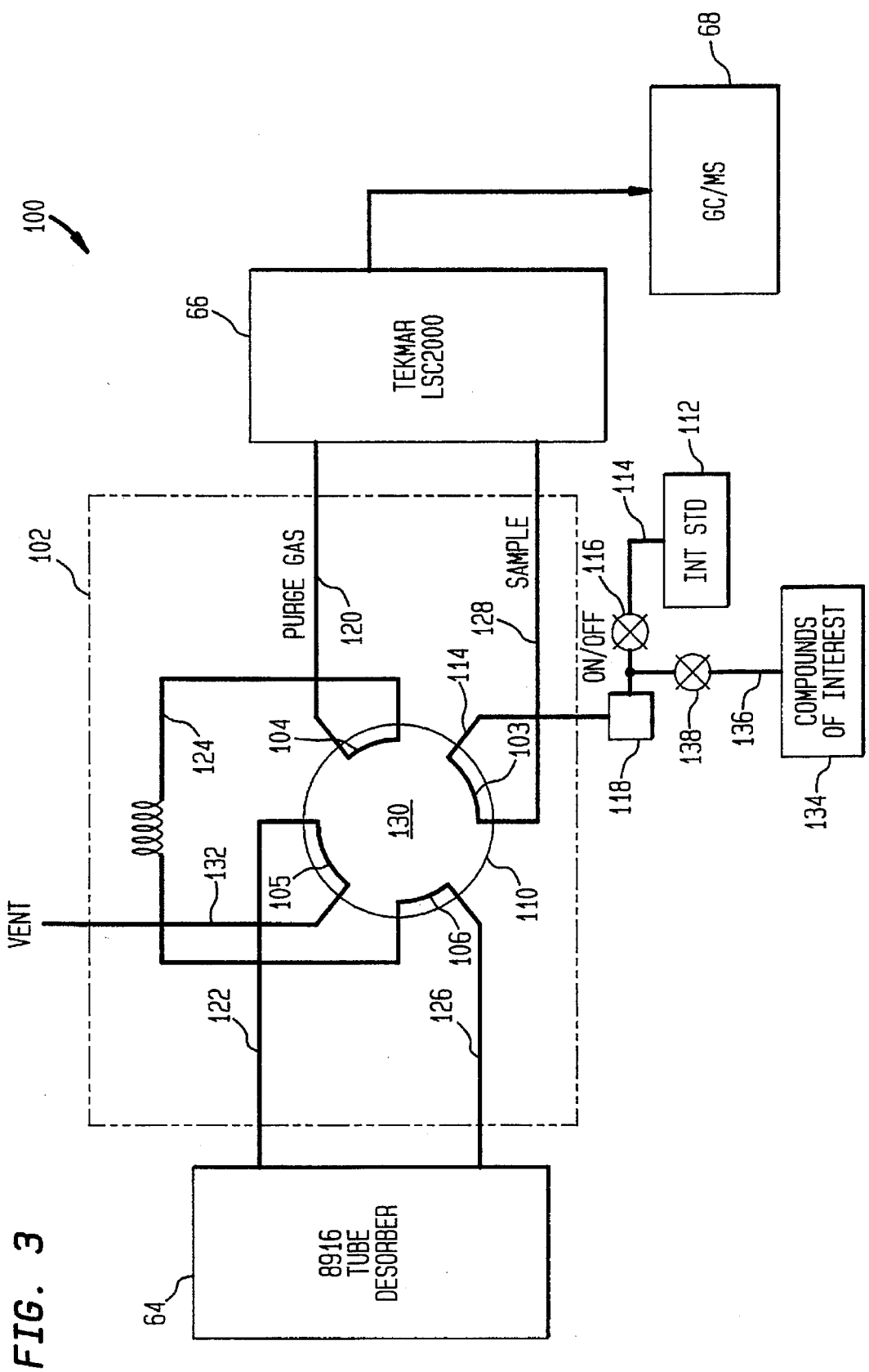
FIG. 3 illustrates gas line connections of a preferred embodiment of an atmospheric sample analyzing apparatus including the spiking apparatus according to the present invention.

FIG. 3 is a diagram illustrating the gas line connections of a preferred embodiment of an atmospheric sample analysis apparatus 100 including the spiking apparatus 102 according to the present invention. Preferably, the spiking device 102 is enclosed in a thermally insulated enclosure, as indicated by the dashed lines. The spiking device 102 is located between a tube desorber 64, such as an Environchem model 8916 tube desorber, and a sample concentrator 66, such as a Tekmar model LSC2000 sample concentrator. The sample concentrator 66 is connected to an analysis device 68 such as a gas chromatograph and/or a mass spectrometer. In this illustration, the sample has already been loaded onto a sorbent tube (not shown) and the sorbent tube is loaded into the tube desorber 64.

The spiking device includes a rotatable 8-port valve 110. The 8-port valve has four conduits: 103, 104, 105, and 106. Each conduit has two ports for establishing gas tight connections with tubes. A reference substance source 112 containing, for example, an internal standard gas is connected to the 8-port valve 110 via a reference substance supply tube 114. This may be a high pressure canister containing pre-mixed solution. The reference substance supply tube 114 may be opened and closed with an on/off switch 116. The on/off switch may be an electrically activated solenoid vane or any other device for opening and closing a tube. The reference supply tube 114 may also have an optional preheating element 118 to heat the reference substance to a predetermined temperature, such as 40° C. The preheating element 118 may be a heating coil wound around the tube 114 or other suitable heating device. The preheating element allows the reference substance always to be delivered to the 8-port valve at a known temperature, thus eliminating any effects of the ambient temperature on the analysis. This provides better accuracy because the temperature of the gas is known and permits greater reproducibility of the analysis. Also, the high pressure canister is connected to the spiking device with gas-tight components. This prevents contamination.

A purge gas delivery tube 120 connects a purge gas source in the sample concentrator 66 to the 8-port valve. A first desorber tube 122 connects the tube desorber 64 and the 8-port valve 110. A fixed volume tube 124 sits between two openings on the 8-port valve 110. The fixed volume tube 124 has a precisely measured, predetermined volume, such as 1 milliliter. A second desorber tube 126 connects the tube desorber 64 and the 8-port valve 110. A sample delivery tube 128 connects the 8-port valve to an input of the sample concentrator 66. A heater 130 may be provided to maintain the spiking device 102 at a predetermined temperature. Preferably, the portions of the desorber tubes 122, 126 and sample delivery tube 128 that extend outside of the heated spiking device 102 are insulated and have heaters and temperature sensors to maintain the entire length of the tubes 122, 126, 128 at a constant temperature. A vent tube 132 connects a port of the 8-port valve to an external vent.

Optionally, a second substance source 134 containing, for example, one or more compounds of interest (such as compounds expected to be found in a sample) is provided. The second substance source 134 is connected to the 8-port valve 110 via a second substance supply tube 136 which connects the reference substance supply tube 114. The second substance supply tube 136 may be opened and closed with a second on/off switch 138. The second on/off switch may be an electrically activated solenoid valve or any other device for opening and closing a tube.

A preferred method of spiking according to the present invention includes the following steps:

1. Mounting the sorbent tube into the tube desorber 64.
2. Filling the fixed volume tube 124 with the reference substance.
3. Spiking the sorbent tube with the reference substance.
4. Desorbing the spiked sample from the sorbent tube into the sample concentrator 66.

Each step is described in detail with reference to FIGS. 4, 5, and 6.

Step 1: First, the sorbent tube having a sample already in it is mounted into a tube desorber 64 in the conventional manner.

Step 2: Second, the 8-valve port 110 is rotated into the position seen in FIG. 4 (if its not already in this position). In this position, the conduits are aligned so that the reference sample delivery tube 114 is connected to a first port of a first conduit 103. The second port of the conduit 103 is connected to one end of the fixed volume tube 124. The second end of the fixed volume tube is connected to a third conduit 105 which is also connected to the vent tube 132. A gas tight passageway is established from the reference substance source 112, through the fixed volume tube 124, to the vent. The reference substance on/off switch 116 is activated, allowing the reference substance to enter the passageway. Any gas or other substance that may be in the fixed volume tube is flushed out the vent 132. The reference substance then fills the fixed volume tube 124 at a known temperature and pressure, so that the amount of gas in the tube may be precisely known. The remaining tubes are not used in this step.

Step 3: Third, the 8-port valve 110 is rotated into the position seen in FIG. 5. In this position, the purge gas delivery tube 120 is connected to a first port of a second conduit 104. The second port of the second conduit 104 is connected to one end of the fixed volume tube 124. The other end of the fixed volume tube 124 is connected to a first port on a fourth conduit 106. The second port of the fourth conduit 106 is connected to one end of the second desorber tube 126. The second end of the second desorber tube 126 connects to the tube desorber 64. At this time, the second desorber tube 126 is an input to the tube desorber 64. A gas tight passageway is established from the purge gas source through the fixed volume tube 124 to the front of the sorbent tube in the tube desorber 64. The purge gas exits the sorbent tube, travels through tubes 122 and 132 (via conduit 105), and exits through the vent.

The purge gas, such as helium or nitrogen, pushes the reference substance through the fixed volume tube 124 into the tube desorber 64 and onto the sorbent tube in the same direction as the sample was loaded onto the tube. The purge gas flow rate is known (i.e., 50 ml/minute) and is applied for a known amount of time (i.e., 2 minute). The total flow volume may be determined by the flow rate x time. Determining the flow volume allows one to know that the total flow is greater than the tube volume, thus insuring that the contents of the loop 124 are delivered to the tube. The sorbent tube is now spiked with a precise amount of reference substance.

Step 4: Fourth, the 8-port valve 110 is rotated into the position seen in FIG. 6. The purge gas delivery tube 120 is connected to the first desorber tube 122 via a third conduit 105. During desorbing, the first desorber tube is used as a tube desorber input. The second desorber tube 126 is connected to the sample delivery tube 128 via a first conduit 103. This second desorber tube 126 is now used as a tube desorber output. A gas tight passage is established from the purge gas source through the sorbent tube in the tube desorber 64 to the sample concentrator 66. The remaining tubes are not used in this step.

The tube desorber has a heater which heats the sample to a predetermined temperature, preferably at a temperature between 170°–250° C., such as 180° C. While the sample is heated up, the purge gas pushes the spiked sample out of the sorbent tube and into the sample concentrator 66. The sample is concentrated for use by the analytical device 68. There may be a second concentrator, such as a cryofocuser, which uses liquid nitrogen to cool the sample to a very low temperature, such as −170° C., before sending the sample to the analytical device 68. Alternatively, the sample may be desorbed directly into the analytical device 68, rather than first going to the sample concentrator 66.

The sample is spiked without manually extracting the reference substance from its container. This eliminates many steps in which human error may be introduced which may adversely affect the accuracy and reproducibility of the analysis. Also, because the reference substance is spiked automatically, high pressure canisters of pre-mixed reference substance may conveniently be used.

Figure 1:
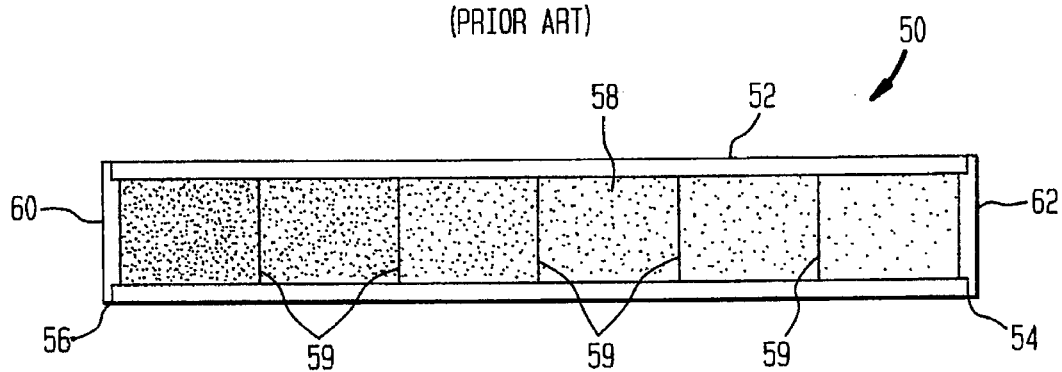
FIG. 1 is a cross-sectional view of a prior art sorbent tube.
Figure 2:
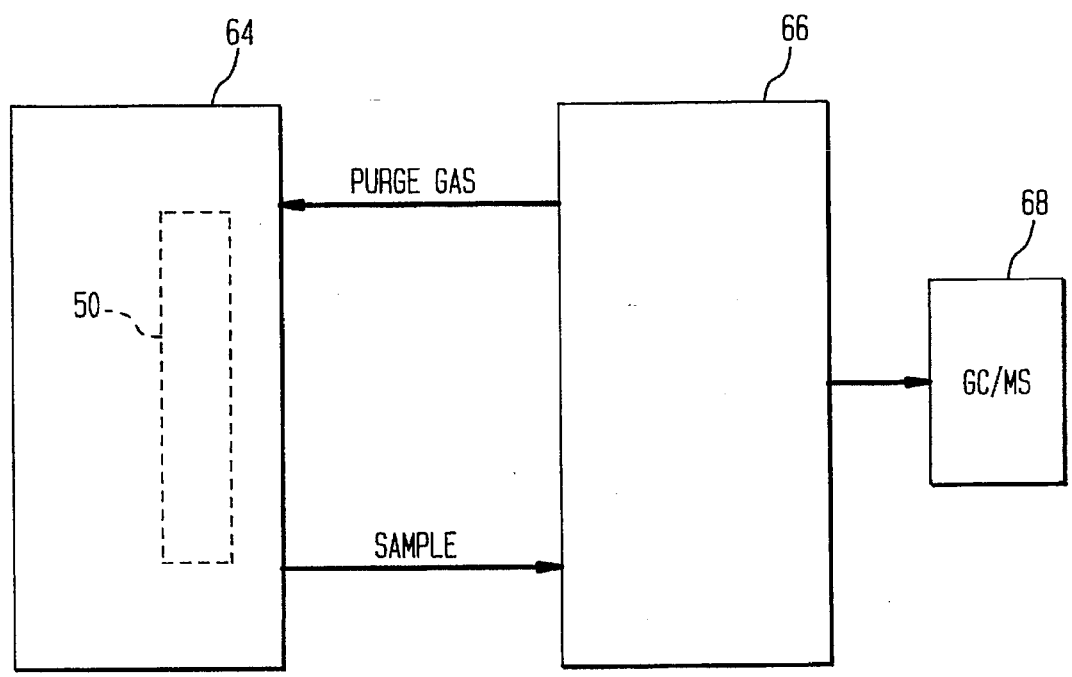
FIG. 2 illustrates a prior art desorbing apparatus.

The inventive method spikes the sample in the same direction as the sample was taken. This is necessary when using multi-component sorbent materials, as seen in FIG. 1. Otherwise, all of the reference substance will be spiked onto the strongest sorbent material, and the heavier molecules may not desorb.

Figure 4:
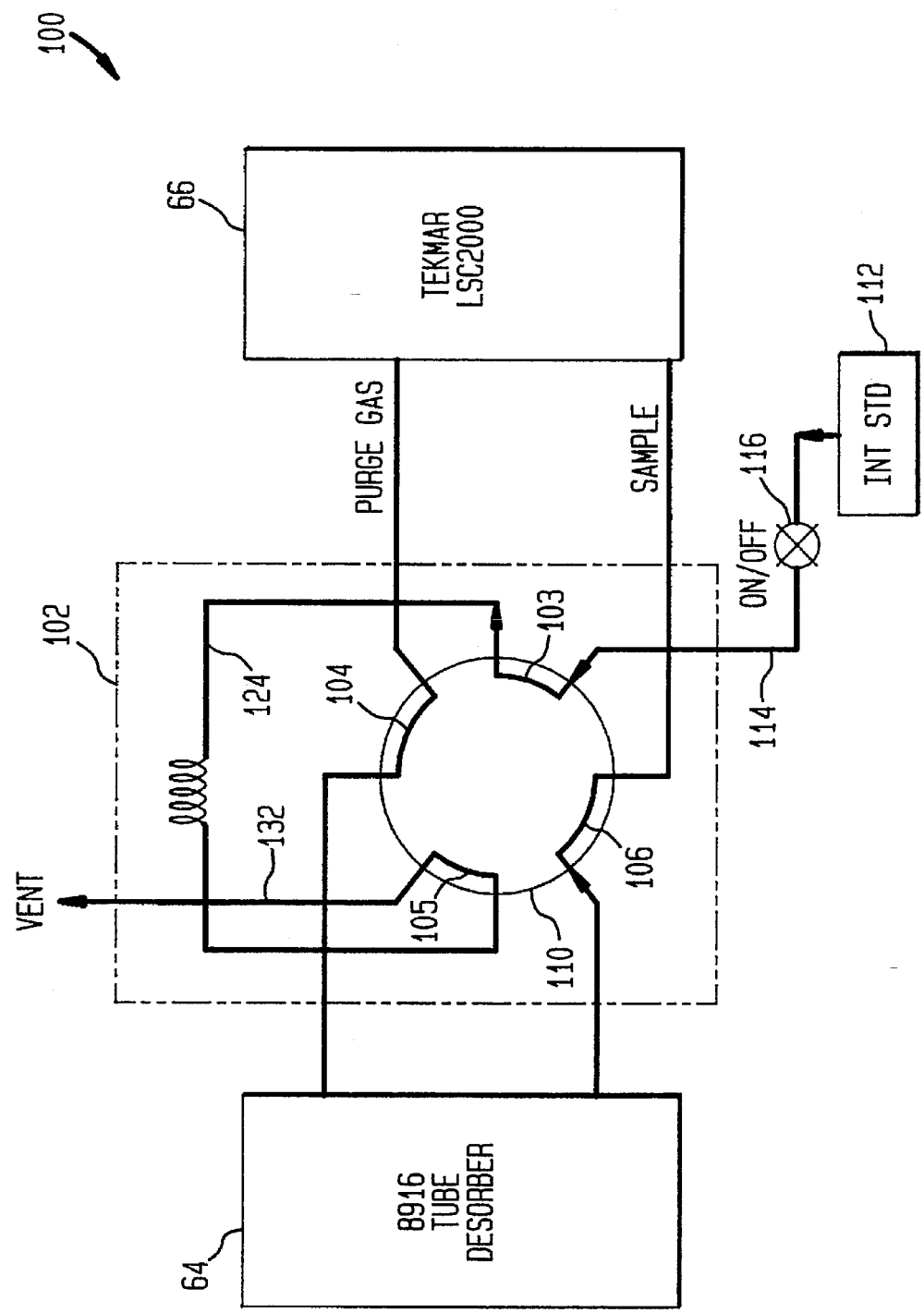
FIG. 4 illustrates the apparatus of FIG. 3 while filling a fixed volume tube with a reference substance.
Figure 5:
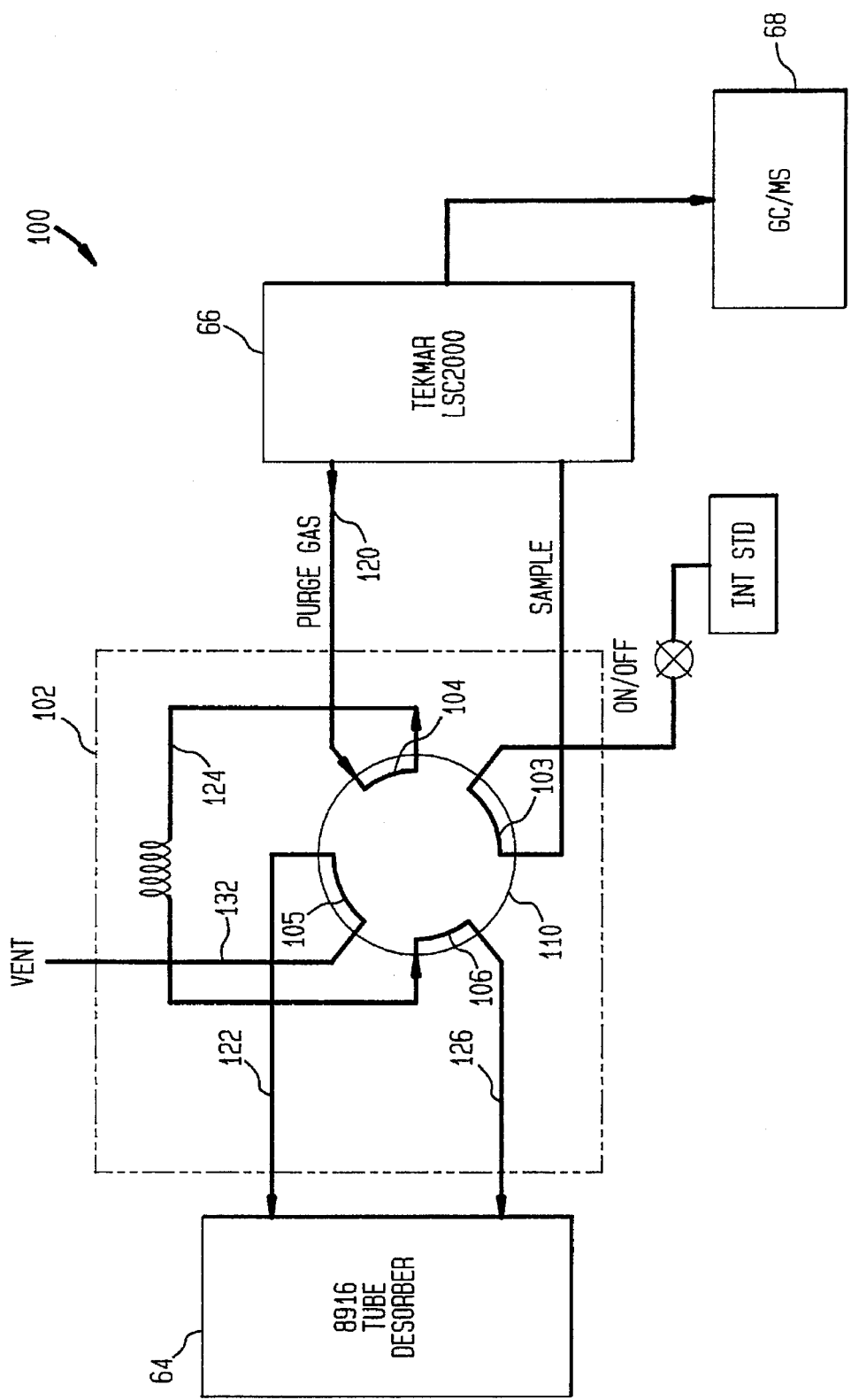
FIG. 5 illustrates the apparatus of FIG. 3 while spiking a sorbent tube with a reference substance.
Figure 6:
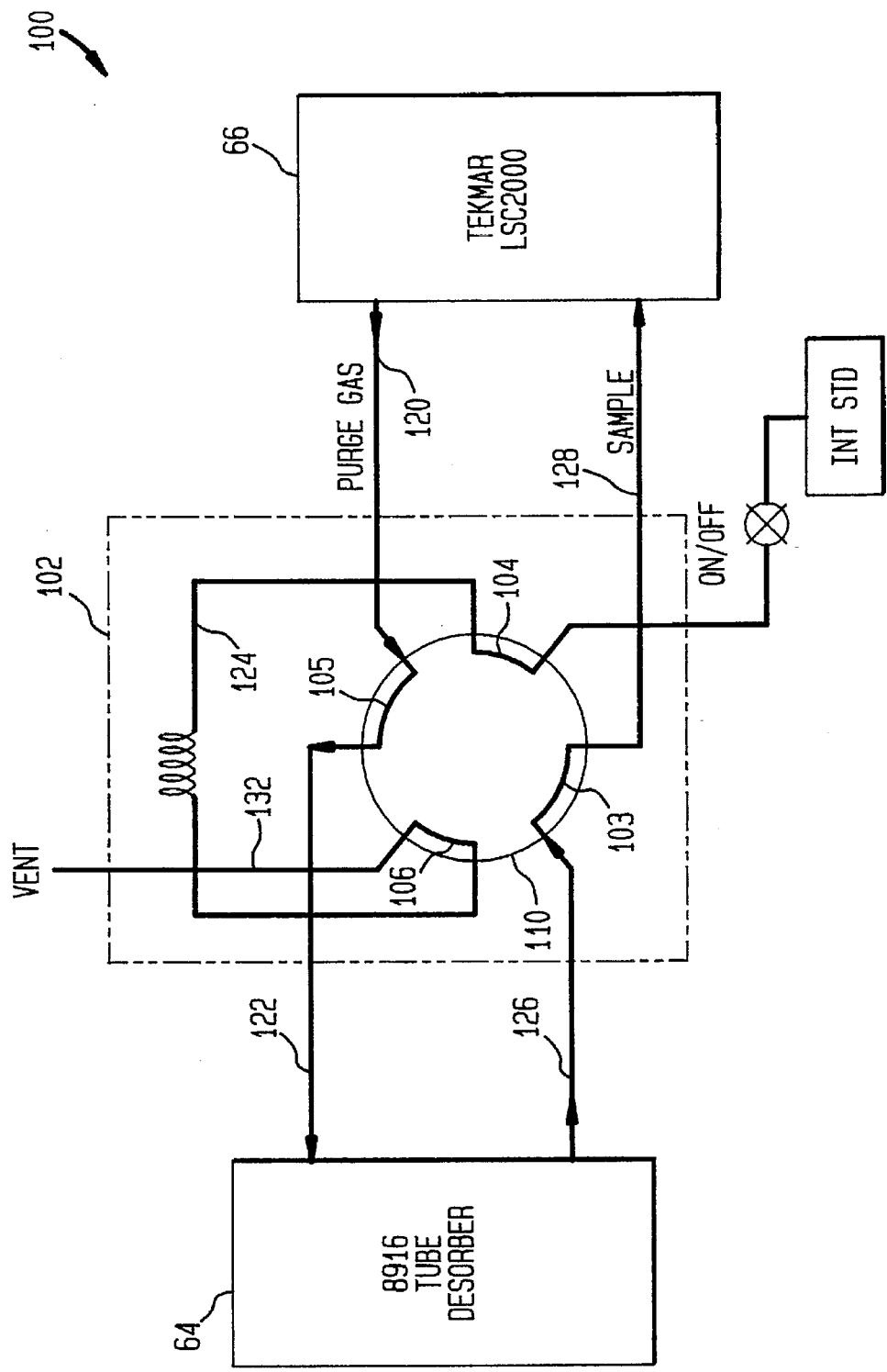
FIG. 6 illustrates the apparatus of FIG. 3 while desorbing a sorbent tube spiked with a reference substance.
Figure 7:
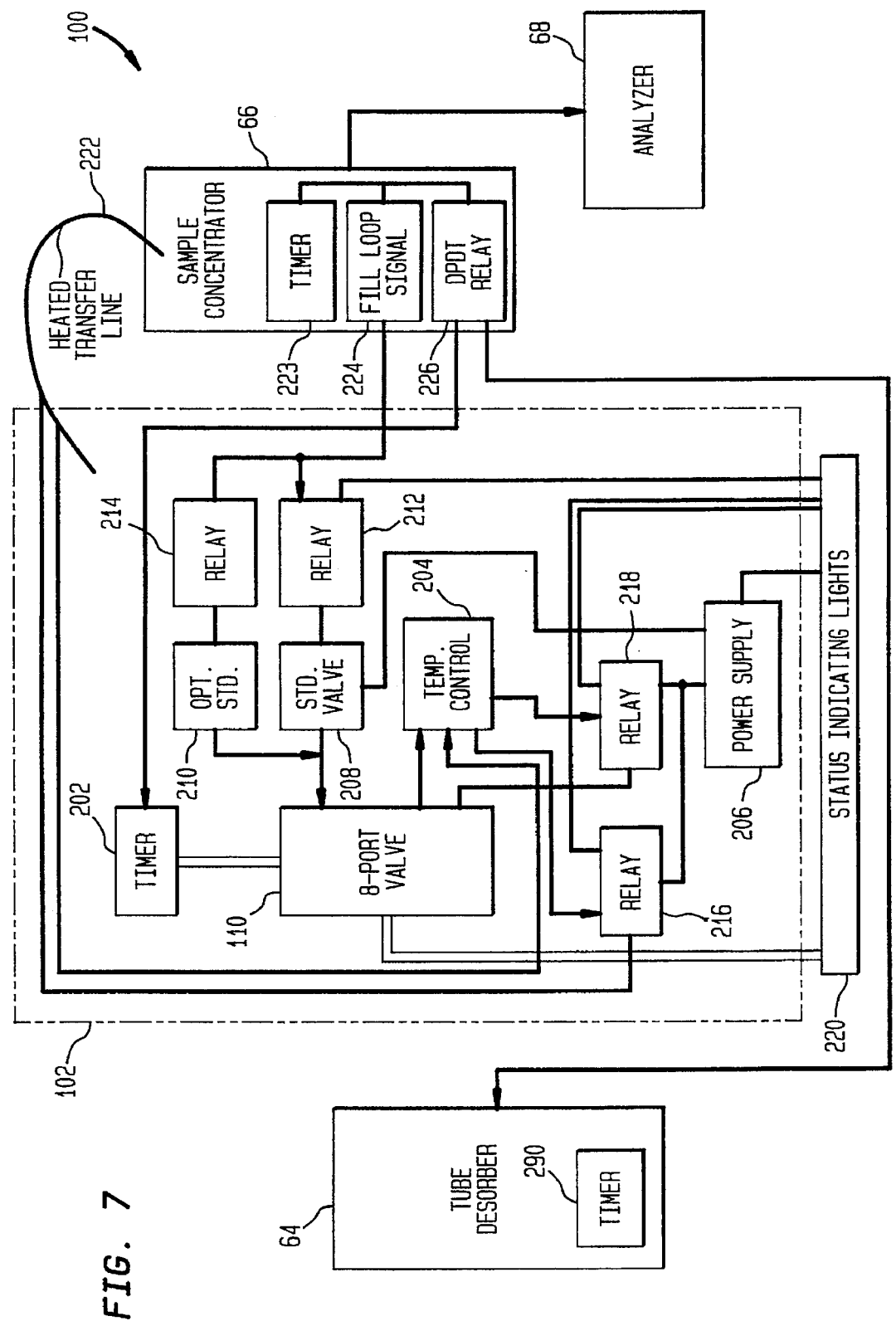
FIG. 7 is a block diagram illustrating electrical connections of a preferred embodiment of an atmospheric sample analyzing device including the spiking apparatus according to the present invention.

FIGS. 4–6 illustrate the 8-port value 110 having two positions. FIG. 7 is a block diagram showing the electrical connections of a preferred embodiment of an atmospheric sample analyzing apparatus 100 including a spiking apparatus 102 according to the present invention.

The spiking device 102 includes a spiking device timer 202, a temperature control 204, a power supply 206, a reference standard valve 208, an optional components of interest valve 210, a number of relays 212, 214, 216, 218, and status indicating lights 220. A heated transfer line 222 is connected from the temperature control 204 to the sample, concentrator 66. The sample concentrator includes a timer 223 which controls a fill fixed volume tube signal circuit 224 and a DPDT relay 226. Each of these components is described in more detail below.

The power supply 206 may be any power supply adequate to provide power to the apparatus. Preferably, the power supply is a +/−15 volts AC, regulated power supply. The 8-port valve is motorized and receives power from the power supply 206. The motor responds to the timer 202 in a manner described below.

The temperature control 204 controls the spiking device heater 130 (see FIG. 3), the heated transfer line 222, and may also control the reference source pre-heater 118. The temperature controller preferably receives the temperatures of the 8-port valve 110 and the transfer line 222 via thermocouples. The temperatures are converted into voltages corresponding to the temperatures. The voltages are compared with a reference voltage for a desired temperature, such as 200° C., in order to keep the compounds in a gaseous state. If the temperature falls below a desired temperature for the heated transfer line 222 or spiking device 102, the temperature controller activates relays 216, 218, that turn on and off power to the resistance wire wrapped around the length of the transfer lines (for heating), or 8-port valve heater 130, respectively.

Figure 8:
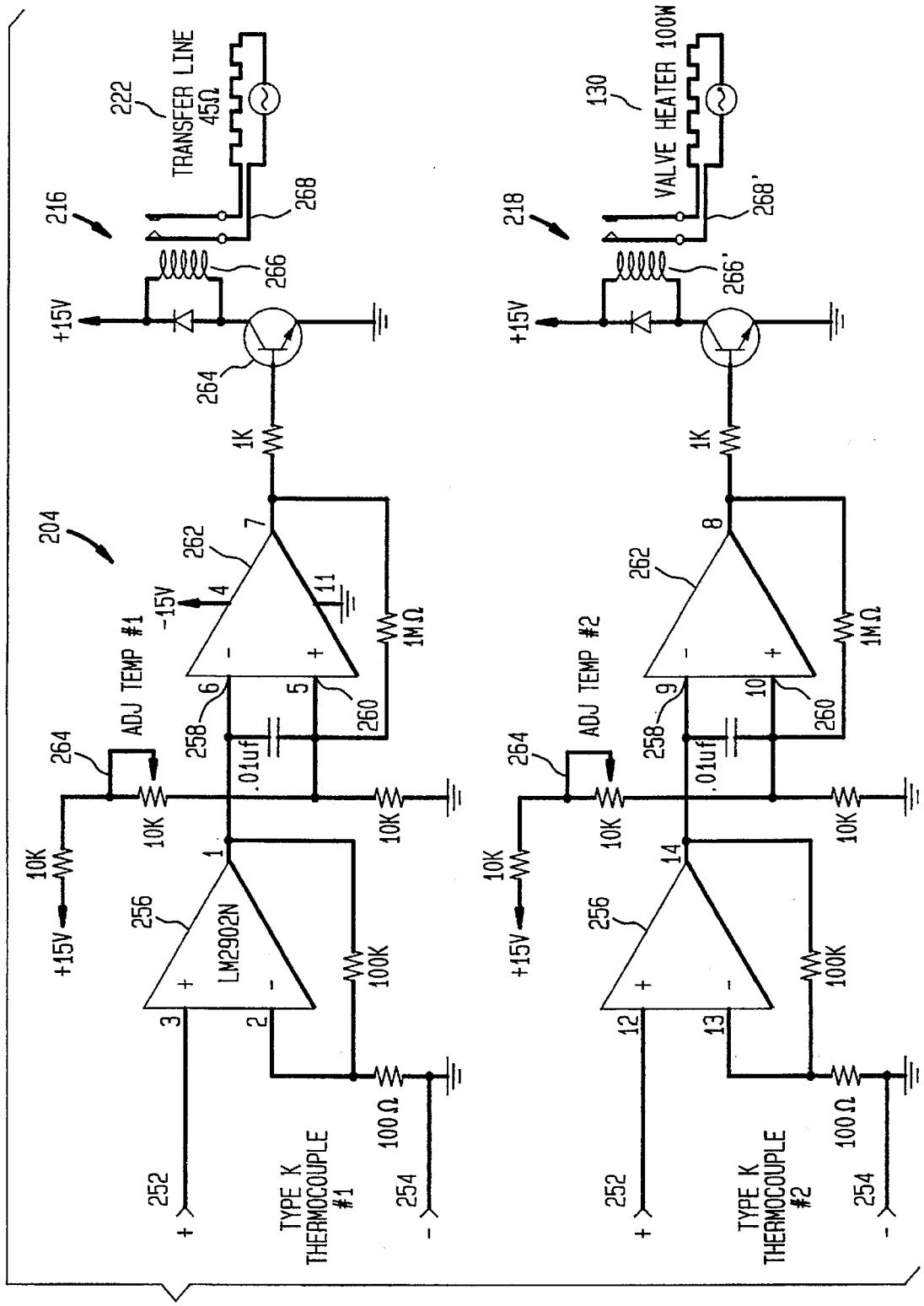
FIG. 8 is a block diagram illustrating a preferred spiking apparatus temperature control circuit.

FIG. 8 is a block diagram of one embodiment of the temperature control 204 according to the present invention. A person skilled in the art readily understands that many other circuits are equally suitable for the temperature control used in the inventive device. Preferably, a thermocouple is connected to a first operational amplifier 156, such as an LM2902N integrated circuit made by National Semiconductor. The output voltages of the thermocouple metals change as the temperature varies, thus changing the input voltages on the terminals 252, 254 of the operational amplifier 256. Changes in the terminal voltage results in a change in the first op amp 256 output. This output change corresponds to the temperature change. The output of the first op amp 256 is applied to the inverting terminal 258 of a second op amp 262.

A reference voltage is applied to the non-inverting terminal 260 of the second op amp. The reference voltage corresponds to a particular temperature and is selected by adjusting a variable resistor 264. When the output voltage of the second voltage exceeds a threshold voltage, a transistor 264 turns on, causing current to flow through a relay inductor 266 (or 266'). When current flows through the inductor, the contacts (268, 268') on relays 216, 218 are connected, providing power to either the transfer line 222 or the valve heater 130. The desired temperatures for the transfer line 222 and the valve heater 130 may be set to different values by adjusting the variable resistors 264 to different settings.

Figure 9:
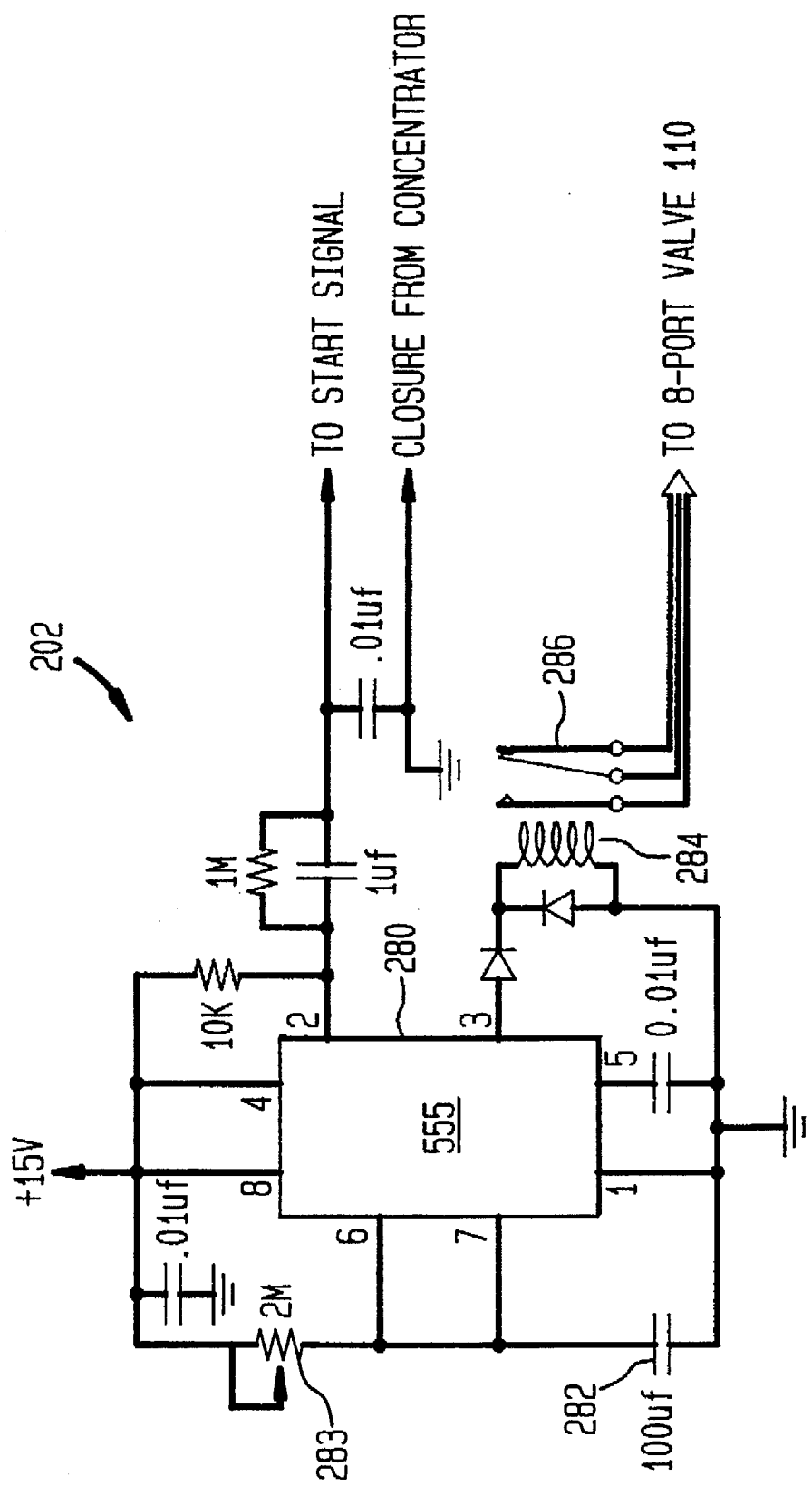
FIG. 9 is a block diagram of a preferred spiking apparatus timing circuit.

The spiking device timer 202 controls the rotation of the 8-port valve. The spiking device tinier primarily controls the length of time that the loop 124 is flushed onto the sample tube. FIG. 9 is a block diagram of a preferred embodiment of the timer 202 according to the present invention. A person skilled in the art readily understands that many other circuits are equally suitable for the tinier used in the inventive device. A timing device 280, such as an RS555 Timer Chip integrated circuit from Radio Shack, may be used. The timing cycle is determined by the RC time constant of a timing capacitor 282 and variable resistor 283. At predetermined times, the timing circuit 202 causes electrical current to flow through an inductor 284. When current flows through the inductor, a relay 284 is activated. The relay determines what position the 8-port valve 110 is in. In a preferred embodiment, the 8-port valve 110 is typically in the position shown in FIGS. 4 and 6. It is only in the position shown in FIG. 5 during the timed cycle controlled by tinier 202.

The method described above is timed using three timers. The first timer 223 is found in the sample concentrator 66, the second is the spiking device tinier 202, and the third a sample tube heater delay tinier 290 found in the tube desorber 64 (see FIG. 7). The DPDT relay 226 in the sample concentrator 66 synchronizes the three timers. The method described above is timed in the following manner.

The sorbent tube is mounted into the tube desorber (step 1), and the timers are initiated. For example, the DPDT relay 226 may send a "start" signal that initiates the timing sequence for the three timers.

Next, the fixed volume tube 124 is to be filled with the reference substance (step 2). The sample concentrator timer 223 activates the fill fixed volume tube signal circuit 224 to generate a "fill" signal. This circuit may be specifically programmed into the sample concentrator timer to activate the "fill" signal. Alternatively, the concentrator timer may use a "pre-heat step" signal as the "fill" signal. A "pre-heat step" signal is generated by the concentrator timer 223 when performing an analysis on soil samples. This step is not used for gas samples, and it may be used to initiate the "fill" step. Another alternative is to program timer 202 or another timer to generate the "fill" signal.

The "fill" signal is applied to a relay 212, which activates the reference substance on/off switch 116 to allow the reference substance to enter the fixed volume tube 124. If the optional "compound of interest" source is to be spiked onto the sorbent tube, this is done either in place of the "fill" step, or after the "fill" and spiking steps are performed for the internal standards and reference compounds.

Next, the sorbent tube is spiked with the reference substance (step 3). The sample concentrator timer 223 has timed the "fill" step and determines that it is complete. The timer activates DPDT relay 226. The DPDT relay 226 initiates the spiking device timer 202 and the sample tube heater delay timer 290.

The spiking device timer 202 turns on the 8-port valve motor to rotate it into the position shown in FIG. 5. The timer 202 times the length of the "spike" step (for example, between 2 and 2½ minutes). The reference substance is spiked onto the sorbent tube. The sample concentrator timer starts and stops the purge gas flow.

The sample tube heater delay timer 290 prevents the tube from being heated until the spike tube cycle is complete. This is done because the tube must be cool when being spiked to prevent the tube from desorbing in the wrong direction during the spiking step, thus preventing the spiked compounds from being correctly trapped by the sorbent material.

At the end of the "spike" step, the timer 202 activates relay 286, which turns on the 8-port valve motor to rotate it into the position shown in FIG. 6. The spiked sample is heated by the tube desorber heater and is desorbed from the sorbent tube into the sample concentrator 66 (step 4). The spiking device timer 202 has timed the "spike" step (including the tube desorber heating delay time) and determines that the step is complete. The sample is then desorbed from the sorbent tube.

The sample concentrator timer maintains a continuous purge gas flow during steps 3 and 4. When the purge gas flow has stopped, the desorbing step is complete.

Once the tube is loaded in the tube desorber (which only takes a few moments), the entire spiking and desorbing process according to the present invention typically takes seven minutes. This results in a much faster process than the prior art liquid solution or gas spiking methods. The method according to the present invention allows several samples (for example, 16 at a time) to be loaded onto the tube desorber without any additional manual steps. Manual spiking may take between 5 to 10 minutes per tube, in addition to the lengthy spiking mixture preparation time. Because the present invention uses air tight components and automatically withdraws the reference solution, pre-mixed pressure canisters may be used. Thus, the method and apparatus according to the present invention provides a significantly faster and more accurate spiking method than was possible using the prior art methods.

An improved method and apparatus for spiking atmospheric samples with reference compounds is described. The method and apparatus have several advantages. There is no mixture preparation, so there is no mixture preparation time. The spiking procedure is automated and greatly reduces the manual effort used in preparing and performing the spiking as compared to the prior art methods. The amount of the reference compounds spiked may be precisely and accurately controlled, resulting in greatly improved reproducibility. There are lower contamination levels and no interference caused by solvents.

The present invention is not limited to the disclosed embodiment, but rather various modifications, substitutions, and structures may be used without departing from the scope of the present invention. For example, a person skilled in the art readily appreciates that the invention may be used in any situation where a known amount of gas is to loaded onto a sorbent tube. For example, this invention may be used for matrix spiking or other quality control procedures.

I claim:

1. A method for spiking a substance onto a sorbent tube having a first end, comprising the steps of:
   a. connecting a substance source with a second tube having a fixed, known volume;
   b. filling the second tube with the substance;
   c. connecting a first end of the filled second tube to a purge gas source and a second end of the filled second tube to the first end of the sorbent tube; and
   d. spiking the substance onto the sorbent tube.

2. The method of claim 1, after the step of spiking, further comprising the step of desorbing the sorbent tube.

3. The method of claim 2, wherein the sorbent tube has a second end and the step of desorbing the sorbent tube comprises the steps of:
   a. connecting the purge gas source to the second end of the sorbent tube;
   b. connecting the first end of the sorbent tube to one of a sample concentrator and an analysis device; and
   c. desorbing the sorbent tube.

4. The method of claim 1, wherein the step of filling the second tube with the substance further comprises maintaining the substance, at a fixed temperature.

5. The method of claim 1, wherein before the step of filling the second tube, preheating the substance to a particular temperature.

6. The method of claim 1, wherein the step of filling the second tube comprises opening a valve connecting the substance source with the second tube.

7. The method of claim 1, wherein before the step of filling the second tube with the substance, flushing the tube with the substance.

8. The method of claim 1, wherein the step of spiking is performed for a fixed time and at a fixed purge gas flow rate.

9. The method of claim 2, wherein before the step of desorbing, heating the substance to a particular temperature.

10. The method of claim 3, further including starting and stopping the step of desorbing at predetermined times.

11. An apparatus for spiking a sorbent tube with a substance, comprising:
   a. a first tub connected to a source of the substance;
   b. a second tube having a fixed, known volume;
   c. a third tube connected to a purge gas source;
   d. a fourth tube connected to an input of a tube desorber; and
   e. a valve configured to selectively connect:
      (1) the first and second tube during a first time; and
      (2) the second, third, and fourth tubes at a second time.

12. The apparatus of claim 11, further comprising:
   a. a fifth tube connected to an output of the tube desorber;
   b. a sixth tube connected to an input of one of a sample concentrator and an analysis device; and
   c. the valve being further configured to connect the third, fourth, fifth, and sixth tubes at a third time.

13. The apparatus of claim 11, further comprising:
   a. a fifth tube connected to a vent; and
   b. the valve being further configured to connect the fifth tube with the first and second tubes during the first time.

14. The apparatus of claim 11, further including a heater configured to maintain the apparatus at a particular temperature.

15. The apparatus of claim 14, further including a heating controller connected to the heater, the heating controller configured to respond to temperature changes in the apparatus.

16. The apparatus of claim 11, further including a preheating element connected to the first tube.

17. The apparatus of claim 11, further including a fifth tube connected to a second substance source, the fifth tube selectively connected to the first tube.

18. The apparatus of claim 11, wherein the valve is an 8-port valve and is configured to rotate.

19. The apparatus of claim 11, further including a timer connected to the valve and configured to time the selective connections of the tubes.

20. The apparatus of claim 19, wherein the timer is responsive to a start signal from a sample concentrator relay.

21. A method for spiking a substance onto a sorbent tube, comprising the steps of:
   a. filling a second tube having a fixed, known volume with the substance;
   b. connecting the second tube between a purge gas source and the sorbent tube; and
   c. using the purge gas, spiking the substance onto the sorbent tube.

22. The method of claim 1, wherein the step of connecting the substance source with the second tube further comprises the step of selectively connecting one of a plurality of substance sources with the second tube.

* * * * *